United States Patent [19]

Brennan

[11] 4,299,957
[45] Nov. 10, 1981

[54] METHOD OF MAKING N-(2-METHOXYETHYL)MORPHOLINE

[75] Inventor: Michael E. Brennan, Austin, Tex.

[73] Assignee: Texaco Inc., White Plains, N.Y.

[21] Appl. No.: 188,165

[22] Filed: Sep. 17, 1980

[51] Int. Cl.$^3$ ............................................ C07D 295/08
[52] U.S. Cl. .................................................... 544/177
[58] Field of Search ......................... 544/177; 568/698

[56] References Cited

U.S. PATENT DOCUMENTS

| 3,033,778 | 5/1962 | Frilette | 568/698 X |
| 3,036,134 | 5/1962 | Mattox | 568/698 |
| 3,140,252 | 7/1964 | Frilette et al. | 568/698 X |
| 3,175,967 | 3/1965 | Miale et al. | 568/698 X |

Primary Examiner—Joseph Paul Brust
Attorney, Agent, or Firm—Carl G. Ries; Robert A. Kulason; James L. Bailey

[57] ABSTRACT

Covers a process of making N-(2-methoxyethyl)morpholine by reacting N-(2-hydroxyethyl)morpholine with an excess of methanol in presence of a silica-alumina catalyst.

1 Claim, No Drawings

4,299,957

METHOD OF MAKING N-(2-METHOXYETHYL)MORPHOLINE

BACKGROUND OF THE INVENTION

1. Field of the Invention

The instant invention generally relates to an improved process for making N-(2-methoxyethyl)morpholine.

2. Prior Art

N-(2-methoxyethyl)morpholine has been found to be a very valuable chemical in the catalyst field. It has been found particularly useful as a polyurethane catalyst. However, many methods of preparing said chemical are relatively expensive, usually involving a metal hydrogenation-dehydrogenation catalyst. One such method involves reaction of morpholine with ethylene glycol monomethyl ether in presence of hydrogen over said metal hydrogenation-dehydrogenation catalyst.

It would be a distinct advance in the art if a method were found of making N-(2-methoxyethyl)morpholine without need to resort to expensive metal hydrogenation-dehydrogenation catalyst and concomitant use of hydrogen. Such is the primary object of the present invention. Other objects will appear hereinafter.

SUMMARY OF THE INVENTION

In accordance with the broad aspects of the present invention N-(2-methoxyethyl)morpholine is produced by reacting N-(2-hydroxyethyl)morpholine with an excess of methanol in presence of a silica-alumina catalyst.

DESCRIPTION OF THE PREFERRED EMBODIMENTS

In accordance with the preferred embodiments to N-(2-methoxyethyl)morpholine is prepared by reacting N-(2-hydroxyethyl)morpholine with an excess of methanol in presence of a silica-alumina catalyst. The reactants are readily available materials and need no further elaboration. Usually the reaction is effected at a relatively high temperature under pressure.

A wide variety of silica-alumina materials may be useful as catalysts here. The silica-aluminas which are most effective as catalysts include those having an alumina content of from about 5 to about 50 wt.% alumina and preferably from about 10 to about 40 wt.% alumina. While silica or alumina utilized alone have proven to be poor catalysts for the process of this invention, the silica-aluminas as herein described effect the reaction in high yields and with high selectivity to the desired product.

While almost of any silica-alumina with an alumina content within the above-mentioned range is effective as a catalyst in the process of this invention, particularly desirable are silica-aluminas with surface areas of from about 50 m$^2$/g to about 700 m$^2$/g.

The silica-alumina catalysts can be employed in any well known form such as a fine powder or as a pellet. Pelletized catalysts are particularly suitable for continuous processes in which the catalyst may be employed as a fixed bed. The particular physical form in which the catalyst is employed is not critical in the process of this invention.

The amount of silica-alumina catalyst employed in the process of this instant invention can be widely varied. In batch processes, silica-alumina catalysts in an amount of from about 1 to about 20 wt.%, based upon the amount of reactants present, have been found satisfactory, with an amount of from about 5 to about 10% being preferred. In a continuous reaction process wherein the catalyst is generally employed as a fixed bed, a weight hourly space velocity (WHSV) of from about 0.1 to 5.0 g/ml catalyst/hour is satisfactory with a space velocity of from about 0.2 to about 2.0 g/ml catalyst/hour being preferred.

The reaction of this invention, as described herein, is carried out substantially in a liquid phase reaction which is conducted at a temperature of from about 200° C. to about 350° C., more often 250°–350° C. It has been found that temperatures in the range of from about 260° to 300° C. are normally sufficient for good yield production of the desired morpholine derivative.

The pressure at which the reaction is carried out can be any pressure sufficient to maintain the reactants substantially in the liquid state. Generally, reaction pressure of from about 10 to about 3,000 psig. have been found satisfactory. It has been found that for typical reaction temperatures the preferable reaction zone pressure is from about 1000 to about 2000 psig.

In practicing the process of this invention a solvent is not required, but may be employed if desired. Whenever a solvent is employed, the solvent should be non-deleterious to the reaction environment and the desired reaction. Examples of suitable solvents include hydrocarbon solvents such as hexane, decane, dodecene, benzene, and the like, and chlorinated aromatic solvents such as chlorobenzene.

The crude reaction product obtained from the process of this invention will contain the desired N-(2-methoxyethyl)morpholine (MEM) in combination with some 2,2'-dimorpholinediethyl ether (DMDEE) and 2,2'-dimorpholine (DMORE) and larger amounts of N-methylmorpholine (NMM).

It has been found that the silica-alumina catalyst may be recovered from the crude reaction mixture and recycled for reuse according to the process of this invention. It is generally preferable to wash the recovered catalyst, for example with methanol and/or water, and dry it prior to recycling it for reuse.

The N-(2-methoxyethyl)morpholine can be recovered from the crude reaction mixture by conventional means, for example distillation, extraction, and the like.

The process of this invention will now be further illustrated in the following examples which are for the purpose of illustration and should not be considered as a limitation on the scope of the invention.

EXAMPLES 1-3

A clean and dry 1 liter stirred stainless steel autoclave was charged with a solution of 262.3 g (2.0 moles) N-(2-hydroxyethyl)morpholine (HEM) and 256.0 g (8.0 moles) methanol and then the catalyst.

A silica-alumina catalyst in an amount of 5.0 wt.% based on weight of reactants was employed. The catalyst used was AEROCAT TA sold by American Cyanamid which contained 74.4% silica, 25.7% alumina, 0.6% other oxides and had a surface area of 550–700 m$^2$/g.

After purging and padding with nitrogen, the autoclave was sealed and then heated to the desired temperature and held for the below indicated length of time. After cooling to room temperature, the autoclave was carefully vented and the reaction mixture recovered. Results are based on glc analysis and Karl Fisher water determination. Products were identified by distillation and spectral characterization and results are shown below in Table I.

TABLE I

| Run. No. | Temp. °C. | Press. psig | t hrs. | % HEM Conv. | NMM | % Selectivity | | |
|---|---|---|---|---|---|---|---|---|
| | | | | | | MEM | DMDEE | DMORE |
| 1 | 280 | 1225-1380 | 4.0 | 66.5 | 23.7 | 62.4 | 6.9 | 1.5 |
| 2 | 270 | 1100-1190 | 4.0 | 43.7 | 21.3 | 64.6 | 7.9 | 1.8 |
| 3 | 260 | 1000-1035 | 4.0 | 33.0 | 21.1 | 66.2 | 8.3 | 1.5 |

The invention is hereby claimed as follows:
1. A process for making N-(2-methoxyethyl)morpholine which comprises condensing N-(2-hydroxyethyl)-morpholine with an excess of methanol in presence of a silica-alumina catalyst having an alumina content of 5-50 wt.% alumina at a temperature of 250° to 350° C., and under a pressure ranging from about 1000 psig to about 2000 psig, the amount of said catalyst ranging from about 1 percent to about 20 percent based on the weight of reactants, and the mole ratio of methanol to N-(2-hydroxyethyl)morpholine ranging from 1.5:1 to 10:1.

* * * * *